United States Patent [19]

Nisato et al.

[11] Patent Number: 4,691,019

[45] Date of Patent: Sep. 1, 1987

[54] AN ANORECTIC AGENT; 4-(3-TRIFLUOROMETHYLPHENYL)-1-(2-CYANOETHYL)-1,2,3,6-TETRAHYDROPYRIDINE

[75] Inventors: Dino Nisato, Pavia; Emilio Crisafulli, Milan; Alberto Bianchetti, Milan; Paolo Carminati, Milan, all of Italy

[73] Assignee: Sanofi, Paris, France

[21] Appl. No.: 811,490

[22] Filed: Dec. 20, 1985

Related U.S. Application Data

[62] Division of Ser. No. 630,969, Jul., 1984, Pat. No. 4,602,024, which is a division of Ser. No. 354,522, Mar. 3, 1982, Pat. No. 4,472,408.

[30] Foreign Application Priority Data

Mar. 11, 1981 [FR] France .................. 81 04890

[51] Int. Cl.⁴ .......................... C07D 211/68
[52] U.S. Cl. ................................ 546/330
[58] Field of Search ......................... 546/330

[56] References Cited

FOREIGN PATENT DOCUMENTS 881894 11/1961 United Kingdom .

Primary Examiner—Jane T. Fan
Attorney, Agent, or Firm—Weingarten, Schurgin, Gagnebin & Hayes

[57] ABSTRACT

The invention relates to 4-(3-trifluoromethylphenyl)-1,2,3,6-tetrahydropyridines of formula

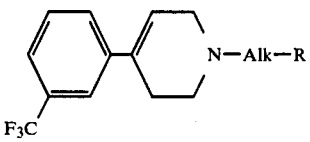

in which R represents a cyano, acetyl or cycloalkyl group of from 3 to 7 carbon atoms and Alk represents a straight or branched alkylene of from 1 to 4 carbon atoms, as well as to the salts thereof, having an anorectic acitivity, to a process for preparing same and to pharmaceutical compositions containing said compounds, useful in the treatment of obesity.

1 Claim, No Drawings

AN ANORECTIC AGENT; 4-(3-TRIFLUOROMETHYLPHENYL)-1-(2-CYANO-ETHYL)-1,2,3,6-TETRAHYDROPYRIDINE

This is a division of application Ser. No. 630,969, filed July 16, 1984, now U.S. Pat. No. 4,602,024 which Application is a division of application Ser. No. 354,522 filed on Mar. 3, 1982, now U.S. Pat. No. 4,472,408.

The present invention relates to novel compounds having anorectic activity.

More particularly, the invention relates to novel 4-(3-trifluoromethylphenyl)-1,2,3,6-tetrahydropyridines of formula

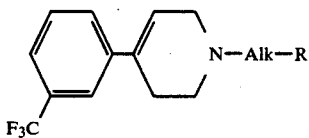

in which R represents a cyano, acetyl or cycloalkyl group of from 3 to 7 carbon atoms and Alk represents a straight or branched alkylene group of from 1 to 4 carbon atoms, as well as to their pharmaceutically acceptable salts, having a noteworthy anorectic activity.

British Pat. No. GB-A-881 894 describes a series of 1-aroylalkyl-4-aryl-1,2,3,6-tetrahydropyridines of general formula

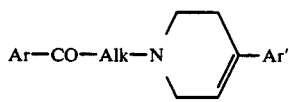

and pharmaceutically useful non-toxic salts thereof, where Ar and Ar' are each a halophenyl radical, alkoxyphenyl radical of less than 11 carbon atoms, or a dimethoxyphenyl, hydroxyphenyl, thienyl, trifluoromethylphenyl or monocyclic aromatic radical of less than 11 carbon atoms and Alk is an alkylene radical containing from 3 to 6 carbon atoms.

One of the processes for preparing the compounds II above provides the reaction of an appropriate ω-(4-aryl-1,2,3,6-tetrahydropyridine)alkanonitrile with an aryl magnesium halide, the decomposition of the resulting complex and the isolation of the product.

The above Patent therefore suggests the possibility of using certain ω-(4-aryl-1,2,3,6-tetrahydropyridine)alkanonitides as intermediates in the preparation of compounds having anticonvulsant C.N.S. depressant and tranquillizing action. However, it describes no 3-trifluoromethylphenyl-1,2,3,6-tetrahydropyridine substituted by a cyanoalkyl group.

It is known that the leading compound having anorectic action is amphetamine which exerts its activity by a central biochemical mechanism of action at the level of the dopaminergic and noradrenergic systems.

Amphetamine and its derivatives have important drawbacks as their central nervous system stimulating effect as well as the possibility of habit-forming and of pharmaco-dependence may constitute a potential danger for the patient.

Studies have therefore been dedicated to the search for amphetamine derivatives which present a dissociation between the stimulant effect and the anorectic action. The introduction of a trifluoromethyl group in the meta position of the phenyl group of ethylamphetamine led to a product, hereinafter designated by its International Non-Proprietary Name "fenfluramine", having excellent anorectic activity, which, instead of being a stimulant, has a certain sedative action.

The advantage of fenfluramine and of its derivatives over amphetamine and its derivatives is due to the different mechanism of action. In fact, anorexia induced by amphatamine seems to be mediated by the release of cerebral noradrenaline, while the anorectic action of the fenfluramine depends on the release of the endogenous serotonin of the central neurons (Ann. C. Sullivan et al. Appetite Regulation and its Modulation by Drugs, Nutrition and Drug Interrelation, 1978, Academic Press, 21–82) and on the inhibition of the serotonin uptake.

However, it is known that fenfluramine, at doses very close to the anorectic dose, induces a significant reduction in the cerebral rates of serotonin (Arch. Intern. Pharmacodyn. Ther. 1967, 170, 276) and that a lasting depletion of serotonin may be considered as a sign of potential neurotoxicity (C. D. Morgan et al. Life Sci. Part I, 11, 83; 1972).

It has now been found that the 4-(3-trifluoromethylphenyl)-1,2,3,6-tetrahydropyridines of formula I hereinabove and their salts show a noteworthy anorectic activity associated with a very low toxicity. From the biochemical standpoint, the compounds of formula I hereinabove, as well as their salts, act as agonists of the cerebral serotonin without inducing any depletion of cerebral serotonin nor stimulation of the central nervous system. More particularly, the compounds of formula I hereinabove show a great affinity for the postsynaptic receptors of the serotonin and, by this direct stimulation of the serotoninergic system, they show anorectic activity without the side effects due to the release of serotonin.

Thus the present invention relates to novel 4-(3-trifluoromethylphenyl)-1,2,3,6-tetrahydropyridines of formula I hereinabove, as well as to their pharmaceutically acceptable salts.

Pharmaceutically acceptable salts include the non-toxic salts derived from mineral or organic acids such as hydrochloride, hydrobromide, succinate, tartrate, citrate, fumarate, maleate, 4,4'-methylenebis-(3-hydroxy-2-naphthoate), hereinafter designated "pamoate", 2-naphthalenesulfonate, hereinafter designated "napsylate", methanesulfonate, hereinafter designated "mesylate", p-toluenesulfonate, hereinafter designated "tosylate", and the like.

According to another of its features, the present invention relates to a process for preparing the 4-(3-trifluoromethylphenyl)-1,2,3,6-tetrahydropyridines of formula I hereinabove and the salts thereof.

Said process is characterised in that the 4-(3-trifluoromethylphenyl)-1,2,3,6-tetrahydropyridine of formula:

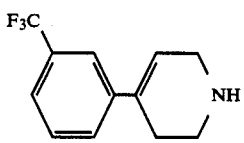

is reacted, in an organic solvent and at a temperature of 20° to 200° C., with a compound of formula X—R, where R has the meaning given hereinabove and X represents a chloro-, bromo- or iodoalkyl group of from 1 to 4 carbon atoms or, only when R is cyano or acetyl, a vinyl group which is nonsubstituted or substituted by 1 or 2 methyl groups or by an ethyl group.

The 4-(3-trifluoromethylphenyl)-1,2,3,6-tetrahydropyridine used as starting material is described in French Pat. Nos. 1 421 208 and 1 459 013.

The preferred organic solvent used is an aliphatic alcohol of from 1 to 6 carbon atoms, such as methanol, ethanol, n-butanol, n-pentanol, but other solvents such as hexane, dimethylformamide, dimethylsulfoxide, sulfolane, acetonitrile, pyridine and the like may be used.

The reaction is advantageously carried out in the presence of a basic condensation agent such as triethylamine, especially when R—X is a halogen derivative.

The reaction temperature may vary between room temperature (about 20° C.) and 200° C. and its duration varies accordingly. After 4 to 5 hours of heating at 100°–150° C., the reaction is generally complete and the end product thus obtained may be isolated according to conventional techniques and optionally converted into its salts by treatment with a solution of the chosen acid in an organic solvent.

According to another aspect, the present invention relates to a process for preparing the compounds of formula I hereinabove in which Alk is straight-chained and R is other than cyano and acetyl, namely compounds of formula:

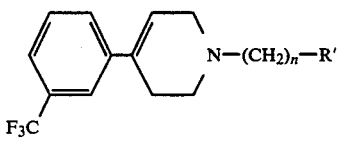

where R' represents a cycloalkyl group containing 3 to 7 carbon atoms and n is 1, 2, 3 or 4, characterized in that a compound of formula

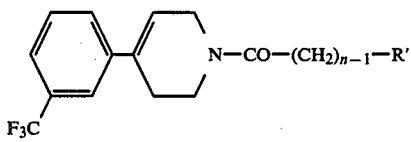

in which R' and n are such as defined hereinabove, is reduced by an aluminum hydride or by a complex hydride of aluminum and lithium in an inert organic solvent at a temperature of from 0° C. to the boiling temperature of the solvent employed and the product thus obtained is optionally converted into its pharmaceutically acceptable salts.

The reduction is carried out according to modi operandi known per se, using aluminum hydride or a complex hydride of lithium and aluminum, such as LiAlH$_4$, LiAlH(OCH$_3$)$_3$ and the like as reduction agent. Operation is generally carried out in an inert solvent such as an ether, such as diethyl ether, tetrahydrofuran, dioxan or 1,2-dimethoxyethane.

According to a preferred modus operandi, operation is carried out with an equimolecular amount of lithium and aluminum hydride LiAlH$_4$ with respect to the starting compound V, at a temperature of 20°–30° C. in diethyl ether and in an inert atmosphere. After about one hour, the reduction is complete and the compound of formula IV is isolated according to conventional techniques in the form of free base or of one of its salts.

The free base thus obtained may be converted into one of its salts by simple salification in an organic solvent such as an alcohol, preferably ethanol and isopropanol, an ether such as 1,2-dimethoxyethane, ethyl acetate or a hydrocarbon such as hexane.

The compounds of formula V hereinabove are prepared by reacting the 4-(3-trifluoromethylphenyl)-1,2,3,6-tetrahydropyridine of formula III with a functional derivative of a carboxylic acid of formula:

where R' and n are such as defined hereinabove, in an organic solvent at a temperature of between −10° C. and the boiling temperature of the solvent employed.

The suitable derivative used may be anhydride, a mixed anhydride, an activated ester or an acid halide preferably chloride. Among the activated esters, the nitrophenyl ester is particularly preferred, but the methoxyphenyl, trityl, benzhydryl esters and the like are also suitable.

The temperature of reaction may vary between 0° C. and the boiling point of the solvent employed, but operation is generally carried out at room temperature or at 30°–50° C. It may be preferable to carry out the reaction in a cold medium when it is exothermic, as when the chloride is used as functional derivative of the benzoic acid of formula VI.

The reaction solvent used is preferably an alcohol such as methanol or ethanol, or a halogenated solvent, such as methylene chloride, dichloroethane, chloroform and the like, but other organic solvents compatible with the reagents used, for example dioxan, tetrahydrofuran or a hydrocarbon such as hexane may also be used.

The reaction may be carried out in the presence of a proton acceptor, for example an alkaline carbonate or a tertiary amine, when hydrochloric acid or another acid is formed during the reaction, but this proton acceptor is not essential for obtaining the final product.

The product which is obtained at the end of the reaction is generally an oil which may be isolated and characterized according to conventional techniques, but which may be used in the crude state for reduction with the hydride.

The 4-(3-trifluormethylhenyl)-1,2,3,6-tetrahydropyridines of the present invention and their salts show a remarkable, selective anorectic activity without giving any amphetamine-like effect. The selectivity of their action is demonstrated by the lack of secondary pharmacological activities, such as sedative or excitant activity and the action inhibiting the locomotor activity.

The anorectic activity was assessed by the method of the food intake in the rat. Female rats weighing 200 g are used, which were trained for 10 days to eat during a period of 4 hours, and selected on the eighth day. At the end of the tenth day, the randomized animals were divided into a "control group" treated by the vehicle alone, and into several "treated groups". Treatment was effected by the intraperitoneal or oral route 30 minutes or 1 hour before presentation of the food and the quantity of food taken during the first hour was then measured.

Table I hereinbelow shows, for seven representative compounds of the invention:
the acute toxicity, expressed as LD$_{50}$ in the rat by the oral or intraperitoneal route (A);

the anorectic activity, expressed as oral or intraperitoneal dose inhibiting by 50% the food intake (ID$_{50}$, B); the ratio between the acute toxicity and the anorectic activity which expresses the therapeutic index related to the acute toxicity (A/B).

The following compounds were used as products representative of the present invention:

4-(3-trifluoromethylphenyl)-1-(2-cyanoethyl)-1,2,3,6-tetrahydropyridine hydrochloride (compound of Example 2);

4-(3-trifluoromethylphenyl)-1-(3-cyanopropyl)-1,2,3,6-tetrahydropyridine hydrochloride (compound of Example 3);

4-(3-trifluoromethylphenyl-1-(4-cyanobutyl)-1,2,3,6-tetrahydropyridine hydrochloride (compound of Example 4);

4-(3-trifluoromethylphenyl)-1-acetonyl-1,2,3,6-tetrahydropyridine hydrochloride (compound of Example 5);

4-(3-trifluoromethylphenyl)-1-(3-oxobutyl)-1,2,3,6-tetrahydropyridine hydrochloride (compound of Example 6);

4-(3-trifluoromethylphenyl)-1-cyclopropylmethyl-1,2,3,6-tetrahydropyridine hydrochloride (compound of Example 7);

4-(3-trifluoromethylphenyl)-1-(2-cyclohexylethyl)-1,2,3,6-tetrahydropyridine hydrochloride (compound of Example 10).

TABLE I

| Compound | Route of administration | A LD$_{50}$ mg/kg | B ID$_{50}$ mg/kg | A/B |
|---|---|---|---|---|
| Example 2 | i.p. | 205.8 | 12.0 | 17.1 |
|  | oral | 254.2 | 9.5 | 26.7 |
| Example 3 | i.p. | 258.5 | 11.1 | 23.3 |
|  | oral | 538.5 | 11.7 | 46 |
| Example 4 | oral | 335.6 | 10.5 | 32.0 |
| Example 5 | i.p. | 165.0 | 10.8 | 15.3 |
| Example 6 | i.p. | 134.2 | 6.5 | 20.6 |
|  | oral | 298.6 | 11.8 | 25.3 |
| Example 7 | i.p. | 135.4 | 5.5 | 24.6 |
| Example 10 | oral | 488.4 | 2.6 | 187.8 |
| fenfluramine | i.p. | 85.6 | 5.4 | 15.8 |
|  | oral | 100.4 | 4.0 | 25.1 |

It follows from this Table that the representative compounds of the present invention show a good anorectic activity with low toxicity. Their efficacy is comparable, from the standpoint of the therapeutic index, to that of the reference compound.

From the biochemical standpoint, the 4-(3-trifluoromethylphenyl)-1,2,3,6-tetrahydropyridines of the present invention and their salts differ from the fenfluramine and its derivatives in their mechanism of action. In fact, the compounds of the present invention are post-synaptic agonists of the serotonin with very weak effects on the pre-synaptic mechanisms, such as the uptake and release of the serotonin, on which, on the contrary, fenfluramine acts. The mechanism of action of the compounds of the present invention involves a remarkable anorectic activity and reduced side effects.

In particular, the compounds of the present invention, in vivo, do not induce any depletion of serotonin at central level. There is therefore less possibility of the lasting use of the compounds of the present invention inducing side effects at central level.

Table II hereinbelow summarizes the cerebral rates of serotonin, in percentage with respect to the controls, after intraperitoneal or oral administration of four representative compounds of the present invention. The determination of the cerebral rates, according to Curzon and Green (Brit. J. Pharmacol. 39, 653, 1970) was effected one hour and/or two hours after administration. Fenfluramine was used as reference material.

TABLE II

| Compound | Route of administration | Dose mg/kg | cerebral rates of serotonin % with respect to controls 1 hr. | 2 hrs. |
|---|---|---|---|---|
| Example 2 | i.p. | 7.5 | — | 128 |
|  |  | 15.0 | 131.0 | 146 |
|  |  | 30.0 | — | 146 |
| Example 6 | i.p. | 3.25 | — | 109 |
|  |  | 7.5 | — | 108 |
|  |  | 15.0 | — | 116 |
| Example 7 | i.p. | 3.25 | — | 111 |
|  |  | 7.5 | — | 123 |
|  |  | 15.0 | — | 119 |
| Example 10 | oral | 1.25 | — | 99 |
|  |  | 2.5 | — | 95 |
|  |  | 5 | — | 101 |
| fenfluramine | i.p. | 5 | 82.9+ | — |
|  |  | 7.5 | 81.6+ | 53.1++ |
|  |  | 10 | 79.0++ | — |

+ significant P < 0.05
++ significant P < 0.01

This Table shows that the products of the present invention, at a dose greater than the anorectic ED$_{50}$, do not reduce the cerebral rates of serotonin, while fenfluramine induces a significant reduction of cerebral serotonin.

The affinity of the compounds of the present invention for the post-synaptic serotonin receptors was determined according to the method of Peroutka and Synder (Molec. Pharmacol. 1979, 16, 687–699) which consists in incubating rat cortex membranes with a fixed concentration of $^3$H-serotonin in the presence of different concentrations of product. Table III hereinbelow shows the molar concentration of five representative compounds of the present invention which give a 50% inhibition of the binding specific to the serotoninergic receptor (IC$_{50}$) namely the measurement of the product ability to interact with the $^3$H-serotonin in the binding at its receptor. Fenfluramine was used as reference compound.

TABLE III

| Compound | $^3$H—serotonin binding (2 μM) IC$_{50}$/M/ |
|---|---|
| Example 2 | 4.3 × 10$^{-7}$ |
| Example 3 | 3.1 × 10$^{-7}$ |
| Example 6 | 1.1 × 10$^{-7}$ |
| Example 7 | 4.1 × 10$^{-7}$ |
| Example 10 | 1.8 × 10$^{-7}$ |
| fenfluramine | >10$^{-5}$ |

This Table shows that the compounds of the present invention have a very good affinity for the post-synaptic serotoninergic receptor while the affinity of the reference compound for the same receptor is much lower.

Thus, according to another of its aspects, the present invention relates to pharmaceutical compositions containing, as active ingredients, 4-(3-trifluormethylphenyl)-1,2,3,6-tetrahydropyridines of formula I hereinabove, as well as to their pharmaceutically acceptable addition salts.

In the pharmaceutical compositions of the present invention for oral, sublingual, sub-cutaneous, intramuscular, intravenous, transdermic or rectal administration, the active ingredients of formula I hereinabove may be administrered in dosage unit forms mixed with conventional pharmaceutical carriers, to animals and to human beings for the treatment of obesity. Among the appropriate dosage forms of administration there are the forms by the oral route such as tablets, capsules, powders, granules and oral solutions or suspensions and the forms of sublingual and oral administration, as well as the forms of parenteral administration useful for subcutaneous, intramuscular or intravenous administration.

In order to obtain the desired anorectic effect, the dose of active ingredient may vary between 0.1 and 100 mg per kg of body weight and per day.

Each unitary dose may contain from 1 to 500 mg of active ingredient in combination with a pharmaceutical support. This unitary dose may be administered 1 to 4 times per day.

When a solid composition is prepared in the form of tablets, the main active ingredient is mixed with a pharmaceutical vehicle such as gelatine, starch, lactose, magnesium stearate, talc, arabic gum or the like. The tablets may be coated with sucrose or other suitable materials or they may be treated in another way so that they have an extended or delayed activity and that they continuously release a predetermined quantity of active ingredient.

A preparation in capsules is obtained by mixing the active ingredient with a diluent and by pouring the mixture obtained into soft or hard capsules.

A preparation in the form of syrup or elixir may contain the active ingredient together with an acaloric sweetening agent, methylparaben and propylparaben as antiseptics, as well as a flavoring agent and an appropriate dye.

Water-dispersible powders or granules may contain the active ingredient mixed with dispersing agents or wetting agents, or suspending agents such as polyvinylpyrrolidone and the like, as well as with sweetening agents or taste correctors.

For rectal application, suppositories are prepared with binding agents melting at rectal temperature, for example cocoa butter or polyethyleneglycols.

For parenteral application, aqueous suspensions, isotonic saline solutions or sterile and injectable particular solutions are used, which contain pharmacologically compatible dispersing agents and/or wetting agents, for example propyleneglycol or butyleneglycol.

The active ingredient may also be formulated in the form of microcapsules, possibly with one or more carriers or additives.

The compositions of the present invention may contain, in addition to the 4-(3-trifluoromethylphenyl)-1,2,3,6-tetrahydropyridines of the present invention or one of their pharmaceutically acceptable salts, other active ingredients such as for example tranquillizers, antidepressants, lipid-lowering drugs, antidiabetic drugs or other drugs which may be used in the treatment of obesity.

The following examples illustrate the invention without, however, limiting the scope thereof.

EXAMPLE 1

A mixture of 0.025 mole of 4-(3-trifluoromethylphenyl)-1,2,3,6-tetrahydropyridine, 3.5 ml of triethylamine and 0.025 mole of chloroacetonitrile in 40 ml of ethanol is heated to reflux for 5 hours. The reaction mixture is cooled, concentrated and the residue is taken up with diethyl ether. The ethereal solution thus obtained is filtered, washed with water and dried over anhydrous sodium sulfate. To the solution thus obtained is added a saturated solution of hydrogen chloride in isopropanol. In this way, the 4-(3-trifluoromethylphenyl)-1-cyanomethyl-1,2,3,6-tetrahydropyridine hydrochloride is obtained which, after crystallization in isopropanol, melts at 169°-172° C. Yield 75% of the theoretical.

EXAMPLES 2 TO 13

By operating as described in Example 1 and by reacting the 4-(3-trifluoromethylphenyl)-1,2,3,6-tetrahydropyridine respectively with 3-chloropropionitrile, 4-chlorobutyronitrile, 5-chlorovaleronitrile, chloroacetone, 1-chloro-3-butanone, cyclopropylmethyl chloride, cyclohexylmethyl chloride, 2-cyclopentyl-1-chloroethane, 2-cyclohexyl-1-chloroethane, 2-cycloheptyl-1-chlorethane, 3-cyclohexyl-1-chloropropane and 2-chloropropionitrile, the compounds of Table IV hereinbelow are obtained.

TABLE VI

| Example | Compound |
|---------|----------|
| 2 | 4-(3-trifluoromethylphenyl)-1-(2-cyanoethyl)-1,2,3,6-tetrahydropyridine hydrochloride which, after crystallization in 95° ethanol, melts at 226–229° C., yield: 50% of the theoretical. |
| 3 | 4-(3-trifluoromethylphenyl)-1-(3-cyanopropyl)-1,2,3,6-tetrahydropyridine hydrochloride which, after crystallization in isopropyl alcohol, melts at 168–170° C. Yield: 46.7% of the theoretical. |
| 4 | 4-(3-trifluoromethylphenyl)-1-(4-cyanobutyl)-1,2,3,6-tetrahydropyridine hydrochloride which, after crystallization in isopropanol, melts at 146–148° C. Yield: 45% of the theoretical. |
| 5 | 4-(3-trifluoromethylphenyl)-1-acetonyl-1,2,3,6-tetrahydropyridine hydrochloride which, after crystallization in isopropyl alcohol, melts at 188–190° C. Yield: 56% of the theoretical. |
| 6 | 4-(3-trifluoromethylphenyl)-1-(3-oxobutyl)-1,2,3,6-tetrahydropyridine hydrochloride which, after crystallization in isopropanol, melts at 173–176° C. Yield: 45% of the theoretical. |
| 7 | 4-(3-trifluoromethylphenyl)-1-cyclopropylmethyl-1,2,3,6-tetrahydropyridine hydrochloride which, after crystallization in acetone, melts at 178–180° C. Yield: 35% of the theoretical. |
| 8 | 4-(3-trifluoromethylphenyl)-1-cyclohexylmethyl-1,2,3,6-tetrahydropyridine hydrochloride which, after crystallization in a 1:4 mixture of isopropanol-ethyl acetate, melts at 217–220° C. Yield: 45% of the theoretical. |
| 9 | 4-(3-trifluoromethylphenyl)-1-(2-cyclopentylethyl)-1,2,3,6-tetrahydropyridine hydrochloride which, after crystallization in isopropanol, melts at 240–245° C. Yield: 39% of the theoretical. |
| 10 | 4-(3-trifluoromethylphenyl)-1-(2-cyclohexylethyl)-1,2,3,6-tetrahydro- |

TABLE VI-continued

| Example | Compound |
|---|---|
| | pyridine hydrochloride which, after crystallization in isopropanol, melts at 252–257° C. Yield: 48% of the theoretical. |
| 11 | 4-(3-trifluoromethylphenyl)-1-(2-cycloheptylethyl)-1,2,3,6-tetrahydropyridine hydrochloride which, after crystallization in isopropanol, melts at 262–265° C. Yield: 40% of the theoretical. |
| 12 | 4-(3-trifluoromethylphenyl)-1-(3-cyclohexylpropyl)-1,2,3,6-tetrahydropyridine hydrochloride which, after crystallization in acetone, melts at 219–222° C. Yield: 25% of the theoretical. |
| 13 | 4-(3-trifluoromethyl)-1-(2-cyano-1-methyl) ethyl-1,2,3,6-tetrahydropyridine hydrochloride. |

EXAMPLE 14

A mixture of 0.03 mole of 4-(3-trifluoromethylphenyl)-1,2,3,6-tetrahydropyridine, of 3.8 ml of triethylamine and 0.03 mole of 3-chloropropionitrile in 40 ml of ethanol is heated to reflux for 4 hours. The reaction mixture is cooled, concentrated, the residue is taken up with diethyl ether and filtered. By treating the ethereal solution thus obtained, containing 4-(3-trifluoromethylphenyl)-1-(2-cyanoethyl)-1,2,3,6-tetrahydropyridine in the form of base, with p-toluenesulfonic acid, maleic acid and, 2-naphthalenesulfonic acid, respectively, the following are obtained:

the tosylate of 4-(3-trifluoromethylphenyl)-1-(2-cyanoethyl)-1,2,3,6-tetrahydropyridine which, after crystallization from acetone, melts at 154°–158° C.;

the maleate of 4-(3-trifluoromethylphenyl)-1-(2-cyanoethyl)-1,2,3,6-tetrahydropyridine which, after crystallization from acetone, melts at 85°–95° C.; and, the napsylate of 4-(3-trifluoromethylphenyl)-1-(2-cyanoethyl)-1,2,3,6-tetrahydropyridine which, after crystallization from acetone, melts at 178°–180° C.

Similarly, the following are obtained:

the maleate of 4-(3-trifluoromethylphenyl)-1-cyclopropylmethyl-1,2,3,6-tetrahydropyridine which, after trituration in diethyl ether, melts at 78°–80° C.;

the napsylate of 4-(3-trifluoromethylphenyl)-1-cyclopropylmethyl-1,2,3,6-tetrahydropyridine which, after crystallization from a mixture of water-acetone, melts at 139° to 142° C.; and, the tosylate of 4-(3-trifluoromethylphenyl)-1-cyanopropylmethyl-1,2,3,6-tetrahydropyridine which, after crystallization from acetone, melts at 86°–88° C.

EXAMPLE 15

0.0263 mole of acrylonitrile is added to a solution of 0.025 mole of 4-(3-trifluoromethylphenyl)-1,2,3,6-tetrahydropyridine in 19 ml of anhydrous ethanol. The reaction mixture is stirred at room temperature for 2 hours, then 50 ml of ethanol and, thereafter, a solution of hydrochloric acid in ethanol are added. The 4-(3-trifluoromethylphenyl)-1-(2-cyanoethyl)-1,2,3,6-tetrahydropyridine hydrochloride identical to the product described in Example 2, is thus obtained by precipitation. Yield: 68.9% of the theoretical.

In the same way, by reacting the 4-(3-trifluoromethylphenyl)-1,2,3,6-tetrahydropyridine with vinylmethylketone, the 4-(3-trifluoromethylphenyl)-1-(3-oxobutyl)-1,2,3,6-tetrahydropyridine hydrochloride, identical to the product described in Example 6, is obtained. Yield: 60.2% of the theoretical.

Under the same operating conditions, by reacting the 4-(3-trifluoromethylphenyl)-1,2,3,6-tetrahydropyridine with crotononitrile, the 4-(3-trifluoromethylphenyl)-1-(2-cyano-1-methyl)ethyl-1,2,3,6-tetrahydropyridine hydrochloride is obtained.

EXAMPLE 16

(a) To a solution of 9.1 g of 4-(3-trifluoromethylphenyl)-1,2,3,6-tetrahydropyridine and of 4.04 g of triethylamine in 40 ml of methylene chloride cooled to 0° C., a solution of 4.2 g of chloride of cyclopropanecarboxylic acid in 20 ml of methylene chloride is added dropwise, while ensuring that the temperature does not exceed 5° C. The reaction mixture is left for 30 minutes at 0°–5° C., then for one hour at room temperature. 200 ml of diethyl ether are added, the mixture is filtered, the organic phase is washed three times with water, dried and evaporated to dryness under reduced pressure. Thus 11.5 g of 4-(3-trifluoromethylphenyl)-1-cyclopropylcarbonyl-1,2,3,6-tetrahydropyridine are obtained: yellow/brown oil containing traces of impurities.

In the same way, by reacting the 4-(3-trifluoromethylphenyl)-1,2,3,6-tetrahydropyridine with cyclohexylcarbonyl, cyclohexylacetyl, 3-cyclohexylpropionyl, cyclopentylacetyl and cycloheptylacetyl chloride in the presence of triethylamine, the following are respectively obtained:

4-(3-trifluoromethylphenyl)-1-cyclohexylcarbonyl-1,2,3,6-tetrahydropyridine, yellowish oil;

4-(3-trifluoromethylphenyl)-1-cyclohexylacetyl-1,2,3,6-tetrahydropyridine, yellowish oil;

4-(3-trifluoromethylphenyl)-1-(3-cyclohexylpropionyl)-1,2,3,6-tetrahydropyridine, yellowish oil;

4-(3-trifluoromethylphenyl)-1-cyclopentylacetyl-1,2,3,6-tetrahydropyridine, crude oil; and 4-(3-trifluoromethylphenyl)-1-cycloheptylacetyl-1,2,3,6-tetrahydropyridine, impure oil.

(b) To a mixture of 1.5 g of LiAlH$_4$ and 60 ml of diethyl ether at 25°–30° C., 11 g of 4-(3-trifluoromethylphenyl)-1-cyclopropylcarbonyl-1,2,3,6-tetrahydropyridine and 50 ml of anhydrous diethyl ether are added in 30 minutes. The product is left for 2 hours with stirring at room temperature, then water is added, the ethereal phase is separated by decantation, dried over anhydrous sodium sulfate and the solvent is evaporated under reduced pressure. The residue oil, constituted by 4-(3-trifluoromethylphenyl)-1-cyclopropylmethyl-1,2,3,6-tetrahydropyridine base, is dissolved in isopropanol and the solution is acidified with hydrogen chloride. In this way is obtained the 4-(3-trifluoromethylphenyl)-1-cyclopropylmethyl-1,2,3,6-tetrahydropyridine hydrochloride which, after crystallization from 50 ml of acetone, melts at 178°–180° C. Yield: 46.5%.

In the same way, the following are obtained:

4-(3-trifluoromethylphenyl)-1-cyclohexylmethyl-1,2,3,6-tetrahydropyridine and its hydrochloride which melts at 217°–220° C.;

4-(3-trifluoromethylphenyl)-1-(2-cyclohexylethyl)-1,2,3,6-tetrahydropyridine and its hydrochloride which melts at 252°–257° C.;

4-(3-trifluoromethylphenyl)-1-(3-cyclohexylpropyl)-1,2,3,6-tetrahydropyridine and its hydrochloride which melts at 219°–222° C.;

4-(3-trifluoromethylphenyl)-1-(2-cyclopentylethyl)-1,2,3,6-tetrahydropyridine and its hydrochloride which melts at 240°–245° C.; and 4-(3-trifluoromethylphenyl)-1-(2-cycloheptylethyl)-1,2,3,6-tetrahydropyridine and its hydrochloride which melts at 262°–265° C.

EXAMPLE 17

To a mixture of 0.152 mole of LiAlH(OCH$_3$)$_3$ and 60 ml of anhydrous diethyl ether at room temperature 0.038 mole of 4-(3-trifluoromethylphenyl)-1-(3-cyclohexylpropionyl)-1,2,3,6-tetrahydropyridine and 50 ml of anhydrous diethyl ether are added in 30 minutes. The product is left for 2 hours with stirring at room temperature, then water is added, the ethereal phase is decanted, dried over anhydrous sodium sulfate and the solvent is evaporated under reduced pressure. The oily residue constituted by 4-(3-trifluoromethylphenyl)-1-(3-cyclohexylpropyl)-1,2,3,6-tetrahydropyridine base, is dissolved in isopropanol and the solution thus obtained is acidified with hydrogen chloride. In this way is obtained the 4-(3-trifluoromethylphenyl)-1-(3-cyclohexylpropyl)-1,2,3,6-tetrahydropyridine hydrochloride which, after crystallization from acetone, melts at 219°–222° C.

EXAMPLE 18

To a mixture of 0.114 mole of AlH$_3$ and 60 ml anhydrous tetrahydrofuran are added 0.038 mole of 4-(3-trifluoromethylphenyl)-1-cycloheptylacetyl-1,2,3,6-tetrahydropyridine and 50 ml tetrahydrofuran. The product is heated to reflux for 2 hours with stirring, then cooled. Water is added, the ethereal phase is decanted, dried over anhydrous sodium sulfate and the solvent is evaporated under reduced pressure. The oily residue constituted by the 4-(3-trifluoromethylphenyl)-1-(2-cycloheptylethyl)-1,2,3,6-tetrahydropyridine base, is dissolved in isopropanol and the solution thus obtained is acidified with hydrogen chloride. In this way is obtained the 4-(3-trifluoromethylphenyl)-1-(2-cycloheptylethyl)-1,2,3,6-tetrahydropyridine hydrochloride which, after crystallization in isopropanol, melts at 262°–265° C.

EXAMPLE 19

Capsules containing the 4-(3-trifluoromethylphenyl)-1-(2-cyanoethyl)-1,2,3,6-tetrahydropyridine hydrochloride and having the following composition:

| Active ingredient | 15 mg |
|---|---|
| lactose | 120 mg |
| Magnesium stearate | 5 mg | are prepared by intimately mixing the above ingredients and by pouring the mixture in capsules of hard gelatine.

EXAMPLE 20

Tablets containing the 4-(3-trifluoromethylphenyl)-1-(2-cyanoethyl)-1,2,3,6-tetrahydropyridine hydrochloride and having the following composition:

| Active ingredient | 20 mg |
|---|---|
| lactose | 100 mg |
| microcrystalline cellulose | 30 mg |
| dried cornstarch | 40 mg |
| magnesium stearate | 5 mg | are prepared by crushing the active ingredient to a particle dimension of 0.4 mm, passing it through a sieve of 0.4 mm mesh opening, mixing the crushed mixture with the other constituents and compressing to form tablets.

In the same way, tablets containing 40 mg of active ingredient are prepared.

EXAMPLE 21

By operating as described in Example 20 hereinabove, tablets having the following composition are prepared:

| Active ingredient | 50 mg |
|---|---|
| lactose | 95 mg |
| cornstarch | 100 mg |
| talc | 4.5 mg |
| magnesium stearate | 0.5 mg |

EXAMPLE 22

10,000 capsules with a content of active substance of 50 mg are prepared from the following constituents: 500 g of 4-(3-trifluoromethylphenyl)-1-(3-oxobutyl)-1,2,3,6-tetrahydropyridine hydrochloride, 495 g of microcrystalline cellulose, 5 g of amorphous silica gel. The above constituents are mixed well and introduced into capsules of hard gelatine of dimension 4.

EXAMPLE 23

A sterile aqueous solution appropriate for parenteral use, in ampules, is prepared, having the following composition:

| Hydrochloride of 4-(3-trifluoromethylphenyl)-1-(2-cyanoethyl)-1,2,3,6-tetrahydropyridine | 30 mg |
|---|---|
| sodium chloride | 5 mg |
| Distilled water | to 2 ml |

EXAMPLE 24

Suppositories are prepared, having the following composition:

| Hydrochloride of 4-(3-trifluoromethylphenyl)-1-(2-cyanoethyl)-1,2,3,6-tetrahydropyridine | 50 mg |
|---|---|
| lactose | 250 mg |
| Witepsol W 45 | to 1.7 g |

The active substance is mixed with the lactose and the mixture is placed uniformly in suspension in the molten mass for suppositories. The suspension is poured into cooled molds to form suppositories weighing 1.7 g.

In the same way, suppositories are prepared, containing 50 mg of 4-(3-trifluoromethylphenyl)-1-cyanomethyl-1,2,3,6-tetrahydropyridine hydrochloride or 50 mg of 4-(3-trifluoromethylphenyl)-1-(3-cyanopropyl)-1,2,3,6-tetrahydropyridine hydrochloride.

EXAMPLE 25

Tablets having the following composition are prepared:

| | |
|---|---|
| hydrochloride of 4-(3-trifluoromethylphenyl)-1-(2-cyano-1-methyl)ethyl-1,2,3,6-tetrahydropyridine | 25 mg |
| lactose | 95 mg |
| corn starch | 45 mg |
| colloidal silica | 2 mg |
| soluble starch | 5 mg |
| magnesium stearate | 3 mg |

The active substance is mixed with part of the adjuvants and the mixture is granulated with a solution of soluble starch in water. After drying the granulate, the rest of the adjuvants is added and tablets are formed by compression.

In the same way, tablets are prepared, containing:

25 mg of 4-(3-trifluoromethylphenyl)-1-cyanomethyl-1,2,3,6-tetrahydropyridine hydrochloride;

25 mg of 4-(3-trifluoromethylphenyl)-1-(2-cyanoethyl)-1,2,3,6-tetrahydropyridine hydrochloride;

25 mg of 4-(3-trifluoromethylphenyl)-1-(3-cyanopropyl)-1,2,3,6-tetrahydropyridine hydrochloride; and, 25 mg of 4-(3-trifluoromethylphenyl)-1-oxobutyl-1,2,3,6-tetrahydropyridine hydrochloride.

EXAMPLE 26

Tablets containing the 4-(3-trifluoromethylphenyl)-1-(3-cyanopropyl)-1,2,3,6-tetrahydropyridine, having the following composition:

| | |
|---|---|
| active ingredient | 20 mg |
| lactose | 100 mg |
| microcrystalline cellulose | 30 mg |
| dried corn starch | 40 mg |
| magnesium stearate | 5 mg | are prepared by using the process described in Example 20.

In the same way, tablets containing 40 mg of active ingredient are prepared.

EXAMPLE 27

20,000 capsules containing 50 mg of active ingredient are prepared from the following constituents:

1000 g of 4-(3-trifluoromethylphenyl)-1-(3-cyclohexylpropyl)-1,2,3,6-tetrahydropyridine hydrochloride, 990 g of microcrystalline cellulose and 10 g of amorphous silica gel. The above constituents are mixed well and introduced into capsules of hard gelatine of dimension 4.

In the same way, capsules are prepared containing 50 mg of 4-(3-trifluoromethylphenyl)-1-(2-cyclopentylethyl)-1,2,3,6-tetrahydropyridine hydrochloride and 50 mg of 4-(3-trifluoromethylphenyl)-1-(2-cyclohexylethyl)-1,2,3,6-tetrahydropyridine hydrochloride respectively.

We claim:

1. 4-(3-trifluoromethylphenyl)-1-(2-cyanoethyl)-1,2,3,6-tetrahydropyridine or a pharmaceutically acceptable acid addition salt thereof.

* * * * *